United States Patent [19]

Prost

[11] 4,283,809
[45] Aug. 18, 1981

[54] SWAB HOLDING TOOL

[76] Inventor: Claude D. Prost, 4009 Port Cleburne La., Hermitage, Tenn. 37076

[21] Appl. No.: 91,456

[22] Filed: Nov. 5, 1979

[51] Int. Cl.³ .............................................. A46B 17/02
[52] U.S. Cl. .................................. 15/145; 15/209 R; 128/269
[58] Field of Search .................. 15/145, 143 R, 144 R, 15/144 B, 209 R, 210 R, 257 R, 218, 208, 211, 146, 176, 425–434; 128/269, 759; 145/61 A, 61 B, 61 J

[56] References Cited

U.S. PATENT DOCUMENTS

| 693,100 | 2/1902 | Bell | 15/209 R |
|---|---|---|---|
| 3,513,830 | 5/1970 | Kalayjian | 128/759 |
| 3,712,296 | 1/1973 | Gradone | 128/759 |
| 4,065,801 | 12/1977 | Leaming | 15/210 RX |
| 4,130,912 | 12/1978 | Sheppard et al. | 15/145 |

FOREIGN PATENT DOCUMENTS 546632  3/1932  Fed. Rep. of Germany ............. 15/428

Primary Examiner—Edward L. Roberts
Attorney, Agent, or Firm—Andrew S. Neely; I. C. Waddey, Jr.

[57] ABSTRACT

The specification discloses a swab holding tool (10) in which a handle (12) includes a passageway (14) with a tube (16) mounted in the passageway (14). The end of the tube (16) away from the handle (12) includes a flaired portion (20) for receiving and holding a swab (22). Indents (18) are formed in the tube (16) for engaging and holding an elongate rod (24) of the swab (22). The swab (22) may be moved in a telescoping action within the tube (16) to a desired fixed position. The handle (12) includes a female recess (15) in the rearward end for inserting of a ramrod into the passageway (14) to eject a broken rod or contaminated swab. Bends (32 and 36) are formed in the tube (16) to provide different angles of attack for cleaning operations.

9 Claims, 5 Drawing Figures

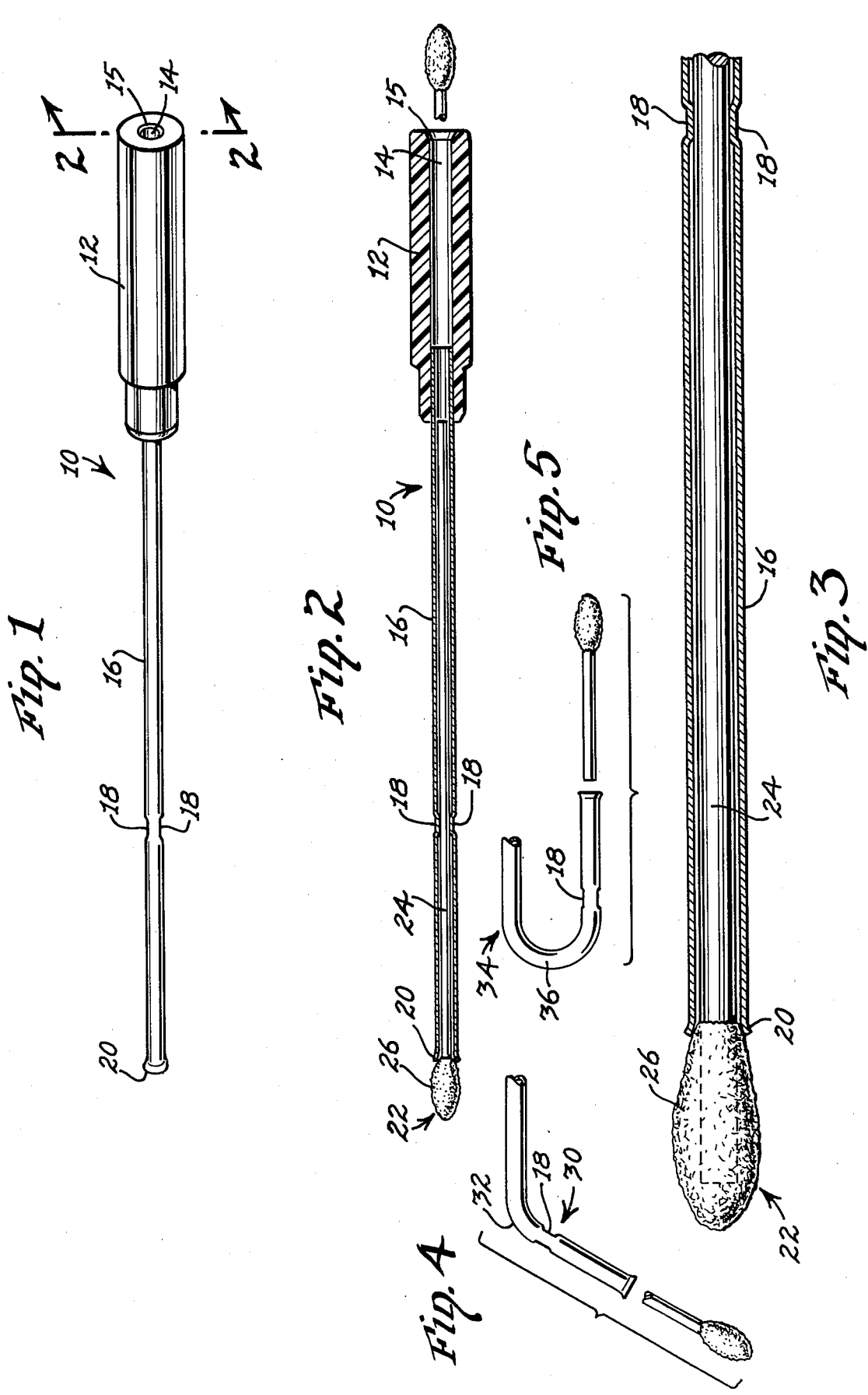

SWAB HOLDING TOOL

FIELD OF INVENTION

The present invention relates to the field of hand-held tools, and particularly relates to a tool for holding a swab for use in cleaning interior components of machinery, electronic devices and the like through narrow passages.

BACKGROUND OF INVENTION

Swabs having absorbent cotton tips are often used in cleaning interior components of machinery, electronic devices and the like through narrow passages in the machinery or housing. For example, cotton swabs soaked in a cleaning fluid are often used to clean the tape sensing heads of a magnetic tape player.

The access to many interior components of electronic or mechanical devices is often through narrow passages of varying length, angles or depth. Many of these narrow passages are longer than the length of the standard size cotton swab. In such case, it is necessary to use an oversized swab, if available, having a longer rod on which the absorbent tip is attached in order to reach the interior surface to be cleaned.

It is cumbersome and generally inconvenient to include cotton swabs of varying length in a tool kit, and often, the oversized cotton swabs have an elongate rod that is too flexible for efficient use in a particular cleaning job desired to be performed. From an expense standpoint, it is inefficient to use an oversized swab to perform a job that a standard size swab could perform equally as well. Thus, it is undesirable to have only oversized swabs in a tool kit.

A need has arisen for a tool swab holder that enables a regular size cotton swab to be used in cleaning jobs that would otherwise require an oversized swab and for use in cleaning operations in which an oversized swab is not suitable. A further need has arisen for a tool swab holder that enables the user to perform delicate cleaning or swabbing more quickly, safely, easily and reliably than could otherwise be performed. For example, the tool of the present invention provides a telescoping feature whereby the length from a handle of the tool to the absorbent swab tip may be varied as desired. Its construction enables commercially available swabs of various diameter or length to be used with one tool.

SUMMARY OF THE INVENTION

The foregoing problems associated with the use of cotton swabs are overcome by the present invention in which a tool is provided for holding a swab having an elongate rod with an absorbent tip formed thereon. The tool is designed for use in cleaning and servicing the interior components of machinery, electronic devices and the like through narrow passages in such devices. An elongate electrically insulated handle dimensioned for being handheld includes a passageway formed in the center of the handle and extending longitudinally through the length of the handle. A tube has an exterior diameter approximately equal to the interior diameter of the passageway. The rearward end of the tube is force-fitted into one end of the passageway, and the forward end of the tool is adapted to receive the elongate rod of the swab. The forward end of the tool is also adapted for securing the elongate rod therein.

In the preferred embodiment, indents are formed proximate to the forward end of the tube and extend inwardly. The distance from the indents to the forward end of the tube is less than the length of the elongate rod of the cotton swab so that the swab can be telescoped in and out of the tube through varying fixed positions. In this manner, the overall length from the handle to the end of the tube can be varied according to the desired use.

The indents in the tube enable the tool to be used with swabs having varying rod diameters. The indents compress and grip the swab rod along a small surface area of the rod relative to the overall rod surface. The compression between the indents and the rod is proportional to the rod diameter, and the rod when compressed by the indents is free to deform into the voids between the indents within the tube.

The rear end of the handle includes a female tapered recess to facilitate insertion of a swab into the handle. The recess fits against and mates with the swab tip so that the swab mounted in the rear of the handle may be used in a scrubbing action.

Also, in the preferred embodiment, the tube is made of steel and has a flared forward end for easily receiving and holding the elongate rod of the cotton swab. Alternatively, the tube may be constructed of an electrically insulating material, such as plastic, for use in environments in which it would be particularly undesirable to make inadvertent electrical contacts.

BRIEF DESCRIPTION OF THE DRAWINGS

The present invention may best be understood by those of ordinary skill of the art by reference to the following Detailed Description when considered in conjunction with the drawings in which:

FIG. 1 is an isometric view of the swab holding tool of the present invention;

FIG. 2 is a cross-section view of the swab holding tool;

FIG. 3 is a detailed cross-sectional view of the forward end of the swab holding tool;

FIG. 4 shows an alternate tool tip bent at a forty-five degree angle; and

FIG. 5 shows another alternate tool tip having a one hundred eighty degree bend.

DETAILED DESCRIPTION

Referring now to the drawings in which like reference characters designate like or corresponding parts throughout the several views, there is shown in FIG. 1 a swab holding tool 10 embodying the present invention. The tool 10 includes a handle 12 that may be constructed from nylon, plastic or any other suitable tool handle material. Preferably, the handle 12 should be made of an electrically insulating material to protect the use of the tool 10 from inadvertent shock.

A passageway 14 is formed in the center of the handle 12 and extends through the length of the handle. The rearward end of the handle 12 contains a female taper 15 for rod insertion and/or retention. A tube 16 extends from one end of the handle 12 and includes indents 18 for and a flared forward end 20, the function of which is hereinafter described.

In FIG. 1, the passageway 14 and the tube 16 are shown as cylindrical. Although a cylindrical shape for these components is used in the preferred embodiment, it will be appreciated that other shapes, such as triangular, square, octagonal, etc., may also function adequately in the invention.

Referring now to FIG. 2, there is shown a cross-sectional view of the tool 10. In this view, it may be seen that the outside diameter of the tube 16 is approximately equal to the inside diameter of the passageway 14. Actually, the diameter of the tube 16 may be slightly greater than the inside diameter of the passageway 14. The rearward end of the tube 16 is press-fitted or force-fitted into the passageway 14. In this manner, the tube is permanently secured on the handle 12. However, if desired, adhesive or conventional fastening devices may be used to secure the tube 16 to the handle 12.

Referring now to the forward end of the tube 16, the opposite end from the handle 12, a swab 22 is shown mounted therein. The swab 22 includes an elongate rod 24 with an absorbent tip 26. Typically, the absorbent tip 26 is cotton, but other suitable absorbent material may be used to form the swab tip, and appropriate material such as paper, wood or plastic is used to construct the rod 24.

The elongate rod 24 has an outside diameter approximately equal to, but slightly smaller than, the inside diameter of the tube 16. Indents 18 are formed in the side walls of the tube 16 and extend inwardly for engaging the elongate rod 24. The resiliency of the rod 24 and the resiliency of the indents 18 serve to secure the elongate rod 24 within the tube 16. The indents 18 are dimensioned to hold and accept rods 24 of varying diameters. The flaired end 20 of the tube 16 is designed to facilitate the insertion and retention of the elongate rod 24 into the tube 16.

The interaction between the swab 22 and the tube 16 may be better appreciated by reference to FIG. 3 in which the end of the tube 16 is shown in a detailed cross-sectional view. In this view, it is apparent that the indents 18 are forced into the sides of the elongate rod 24 to secure the rod within the tube 16. The dimension of the tube 16 is selected sufficiently small to prevent the absorbent tip 26 from being inserted into the tube. However, if the swab 22 or any part thereof is inserted entirely within the tube 16, it may be appreciated by reference to FIG. 2, that the swab 22 may be ramrodded out of the tube 16 by inserting a ramrod through the passageway 14 in the handle 12.

The indents 18 should be positioned sufficiently near the flaired end 20 of the tube 16 so that the distance from the indents to the flaired end is less than the length of the elongate rod 24 of the swab 22. In this construction, the swab 22 may be telescoped outwardly from the position shown in FIG. 2 until the end of the elongate rod 24 reaches the indents 18. When released, the indents 18 will hold the swab in the telescoped position. Thus, this construction allows the user to vary the overall length from the handle 12 to the absorbent tip 26 of the swab 22.

The rod 24 may deform into the voids within the tube 16 between the indents 18. In this construction, the tube 16 will accept and hold rods 24 of a more greatly varying diameter than if the inside diameter of the tube 16 was sized to frictionally engage the rod.

This telescoping feature makes the tool 10 ideally suited for intricate cleaning operations. For example, in cleaning a delicate electronic device, it may be desirable to rest one's hand against the face or the housing of the electronics. In such case, the swab 22 may be telescoped to a position so that the length from the handle 12 to the absorbent tip 26 is equal to the length from the housing to the particular electronic part to be cleaned. When the swab 22 is in this telescoped position, the tool 10 may be grasped by the handle 12 with one's hand resting against the housing, and cleaning motions may be accomplished entirely by finger movements.

The tool 10 may also be used to apply or remove powders and liquids including heavy pastes from various types of surfaces. For example, paints, solvents, acids, greases, polishes, etc., may be applied or removed using the tool 10.

The tube 16 is preferably constructed from rigid tempered stainless steel to provide the rigidity and a thin wall for balance and feel that is required in typical servicing operations. However, it will be appreciated that plastic or other electrically insulating material may also be used in constructing the tube 16. Such electrically insulating materials are desirable when the tool 10 is to be used in an electrically hazardous environment, such as cleaning a television or a stereo.

An alternate forward end 30 for the tube 16 is shown in FIG. 4. The forward end 30 includes a forty-five degree bend 32 to provide a desired angle of attack. Likewise, an alternate forward end 34 is shown in FIG. 5 having an one hundred eighty degree bend 36 to provide another desired angle of attack. The embodiments illustrated in FIGS. 4 and 5 are examples of different possible configurations of the tool 10 that may be used for servicing hard-to-reach parts and surfaces. It will be understood that except for the bends 32 and 36, the tools shown, in part, in FIGS. 4 and 5 are constructed substantially as shown in FIGS. 1, 2 and 3.

Although particular embodiments of the present invention have been described in the foregoing detailed description, it is understood that the invention is capable of numerous modifications, rearrangements and substitutions of parts without departing from the spirit of the invention.

I claim:

1. A tool for holding a swab having an elongate rod with an absorbent tip for use in cleaning interior components of machinery, electronic devices and the like through narrow passageways, comprising:
    an elongate electrically insulated handle dimensioned for being handheld;
    a passageway formed in said handle and extending longitudinally through the length thereof;
    a tube having an exterior diameter approximately equal to the interior diameter of said passageway and having a forward and a rearward end, the rearward end of said tube being secured in said passageway;
    the forward end of said tool being adapted to receive the elongate rod of the swab, and
    at least one indent formed in said tube and extending inwardly with respect to said tube for securing the elongate rod in the forward end of said tube.

2. The tool of claim 1 wherein said indent comprises a plurality of indents formed in said tube and extending inwardly, said indents being formed proximate to the forward end of said tube so that the distance from the forward end of said tube to said indents is less than the length of the elongate rod so that the elongate rod of the swab can be telescoped within said tube to varying positions, whereby the distance from the absorbent tip to said handle may be varied to facilitate use of the tool.

3. The tool of claim 1 wherein the forward end of said tube is flaired for receiving and holding the elongate rod of the swab.

4. The tool of claim 1 wherein said tube is constructed of steel.

5. The tool of claim 1 wherein said tube is constructed of electrically insulating material.

6. The tool of claim 1 wherein said tube is constructed of plastic.

7. The tool of claim 1 wherein said handle includes a rearward end with a female recess formed in said rearward end about said passageway to facilitate insertion of the rod into said passageway and for engaging and holding the absorbent tip.

8. A tool for holding a swab having an elongate rod with an absorbent tip for use in cleaning interior components of machinery, electronic devices and the like through narrow passageways, comprising:
 an elongate electrically insulated handle dimensioned for being handheld;
 a passageway formed in the center of said handle and extending longitudinally through the length thereof;
 a tube having an exterior diameter approximately equal to the interior diameter of said passageway and having a forward and a rearward end, the rearward end of said tube being force-fitted into one end of said passageway;
 the forward end of said tool being adapted to receive the elongate rod of the swab,
 means for securing the elongate rod in the forward end of said tube, and
 a forty-five degree bend formed in the forward end of said tube to provide a desired angle of attack for cleaning and servicing operations.

9. A tool for holding a swab having an elongate rod with an absorbent tip for use in cleaning interior components of machinery, electronic devices and the like through narrow passageways, comprising:
 an elongate electrically insulated handle dimensioned for being handheld;
 a passageway formed in the center of said handle and extending longitudinally through the length thereof;
 a tube having an exterior diameter approximately equal to the interior diameter of said passageway and having a forward and a rearward end, the rearward end of said tube being force-fitted into one end of said passageway;
 the forward end of said tool being adapted to receive the elongate rod of the swab;
 means for securing the elongate rod in the forward end of said tube, and
 a one hundred eighty degree bend formed in the forward end of said tube to provide a desired angle of attack for cleaning and servicing operations.

* * * * *